US00PP36873P3

(12) United States Plant Patent
Bourne

(10) Patent No.: US PP36,873 P3
(45) Date of Patent: Aug. 5, 2025

(54) GRAPEVINE PLANT NAMED 'SV34-130-92'

(50) Latin Name: *Vitis vinifera*
Varietal Denomination: SV34-130-92

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,163

(22) Filed: Aug. 26, 2024

(65) Prior Publication Data

US 2025/0081869 P1 Mar. 6, 2025

Related U.S. Application Data

(60) Provisional application No. 63/628,957, filed on Sep. 5, 2023.

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 5/08; A01H 5/00; A01H 6/88
See application file for complete search history.

(56) References Cited

U.S. PATENT DOCUMENTS

PP3,106 P * 4/1972 Garabedian ..... Plt./207
PP24,531 P3 * 6/2014 Bourne ..... A01H 6/88 Plt./207
PP35,650 P2 * 2/2024 Barba ..... A01H 6/88 Plt./207

* cited by examiner

*Primary Examiner* — June Hwu
(74) *Attorney, Agent, or Firm* — Eric C. Cole; Baker Manock & Jensen, PC

(57) ABSTRACT

A new and distinct variety of grapevine plant named 'SV34-130-92' particularly characterized by its medium, green skinned berries that have a muscat flavor and which ripen in early July in the McFarland, California area.

2 Drawing Sheets

Latin name of the genus and species of the plant claimed: The plant claimed relates to a new and distinct variety of *Vitis vinifera*.

Variety denomination: The plant claimed shall be known as 'SV34-130-92'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV34-130-92'. As used herein, 'grapevine' refers to all plant parts including, vines, canes, tendrils, leaves, fruit and roots of 'SV34-130-92'. Grapevine named 'SV34-130-92' is the result of an effort to produce an early ripening, green, seedless table grape with fruit characteristics superior to currently available green grape cultivar 'Sugraone' (U.S. Plant Pat. No. 3,106). This new cultivar originated from a cross conducted in May 2013 near McFarland, California between female grapevine plant selection 'SV16-72-83' (unpatented) and pollen parent grapevine 'SV21-66-158' (U.S. Plant Pat. No. 24,510). Resultant ovules from the cross were harvested 42 days after pollination and cultured on 'Mccown's Woody Plant Medium'. Subsequently, the resultant embryonic plants were cultured in the same medium in the laboratory under twelve hours of light from light emitting diodes at 29° C. The seedlings from this effort were transplanted to the greenhouse in November of 2013 and grown in the greenhouse at 29° C. with 12 hours illumination under high pressure sodium vapor lamps. The seedling population was planted in the field in the spring of 2014 near McFarland, California. The new grapevine was selected from this seedling population on Jun. 26, 2015. It was then propagated by cuttings and bench grafted to 'Freedom' (unpatented) rootstock in 2016 near McFarland California. The present invention has been found to retain its distinctive characteristics through two successive asexual propagations.

Grapevine named 'SV34-130-92' differs from its female parent grapevine 'SV16-72-83' (unpatented) in that 'SV34-130-92' has berries that are green skinned while 'SV16-72-83' has black skinned berries.

Grapevine named 'SV34-130-92' differs from its male parent grapevine 'SV21-66-158' (U.S. Plant Pat. No. 24,510) in that 'SV34-130-92' has very crisp and firm berries that exceed the crispness and firmness of the berries produced by 'SV21-66-158'.

Grapevine named 'SV34-130-92' most closely resembles commercially available grapevine 'SV21-66-226' (U.S. Plant Pat. No. 24,531) but differs from it in that grapevine named 'SV34-130-92' has oblong berries which ripen in early July whereas grapevine 'SV21-66-226' (U.S. Plant Pat. No. 24,531) has ovate berries which ripen in mid August.

SUMMARY OF THE INVENTION

The following are the most outstanding and distinguishing characteristics of the ripe fruit of this new variety when grown under normal horticultural practices near McFarland, California:

a. Green skinned berries.
b. Crisp berry texture; and
c. Medium sized, oblong berries with muscat flavor.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from a plant that is two (2) years old grown in a field near McFarland, California in 2015.

DETAILED BOTANICAL DESCRIPTION

Figure 1:
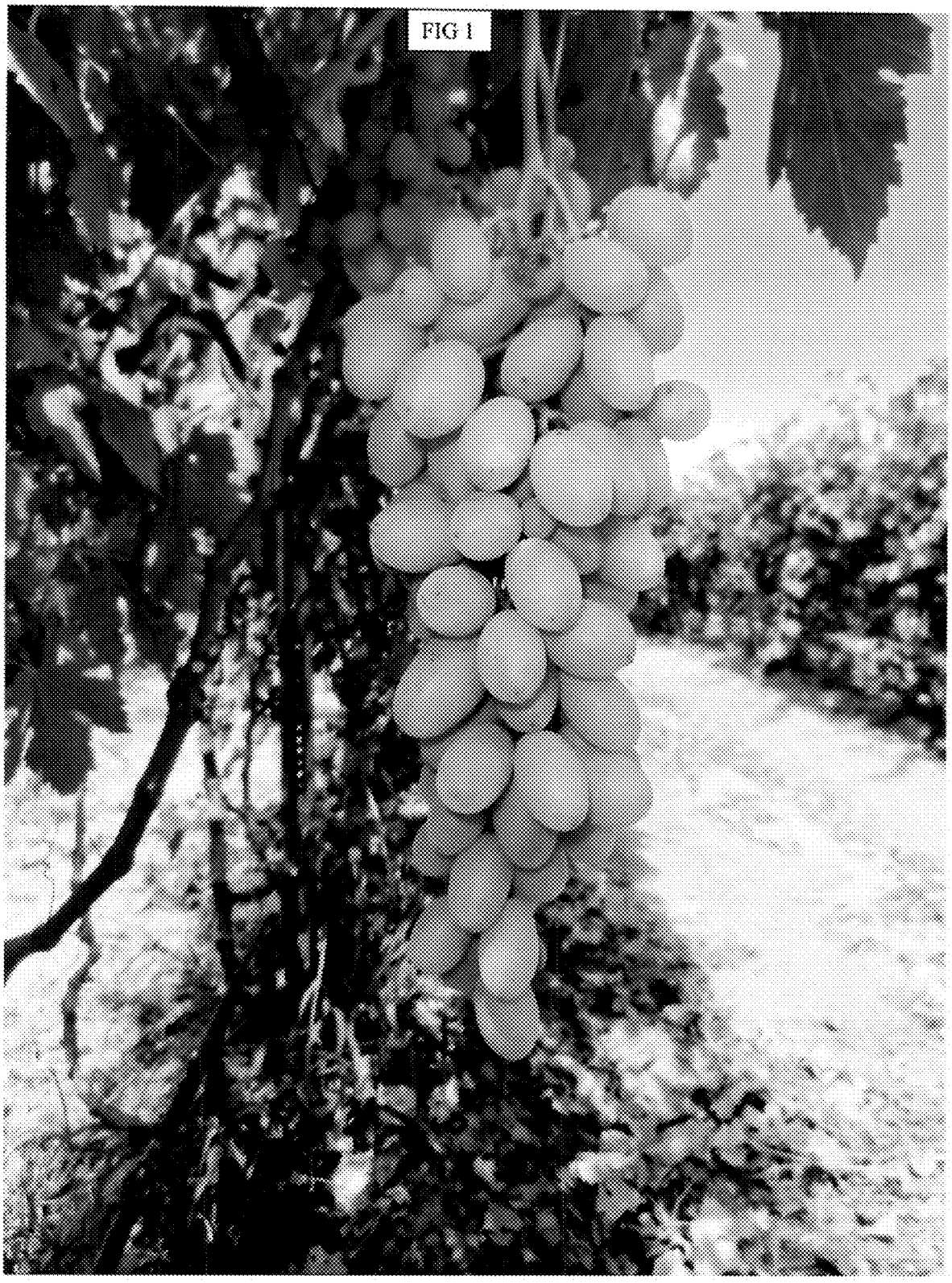
FIG. 1 Fruit cluster on seedling vine of grapevine named SV34-130-92.
Figure 2:
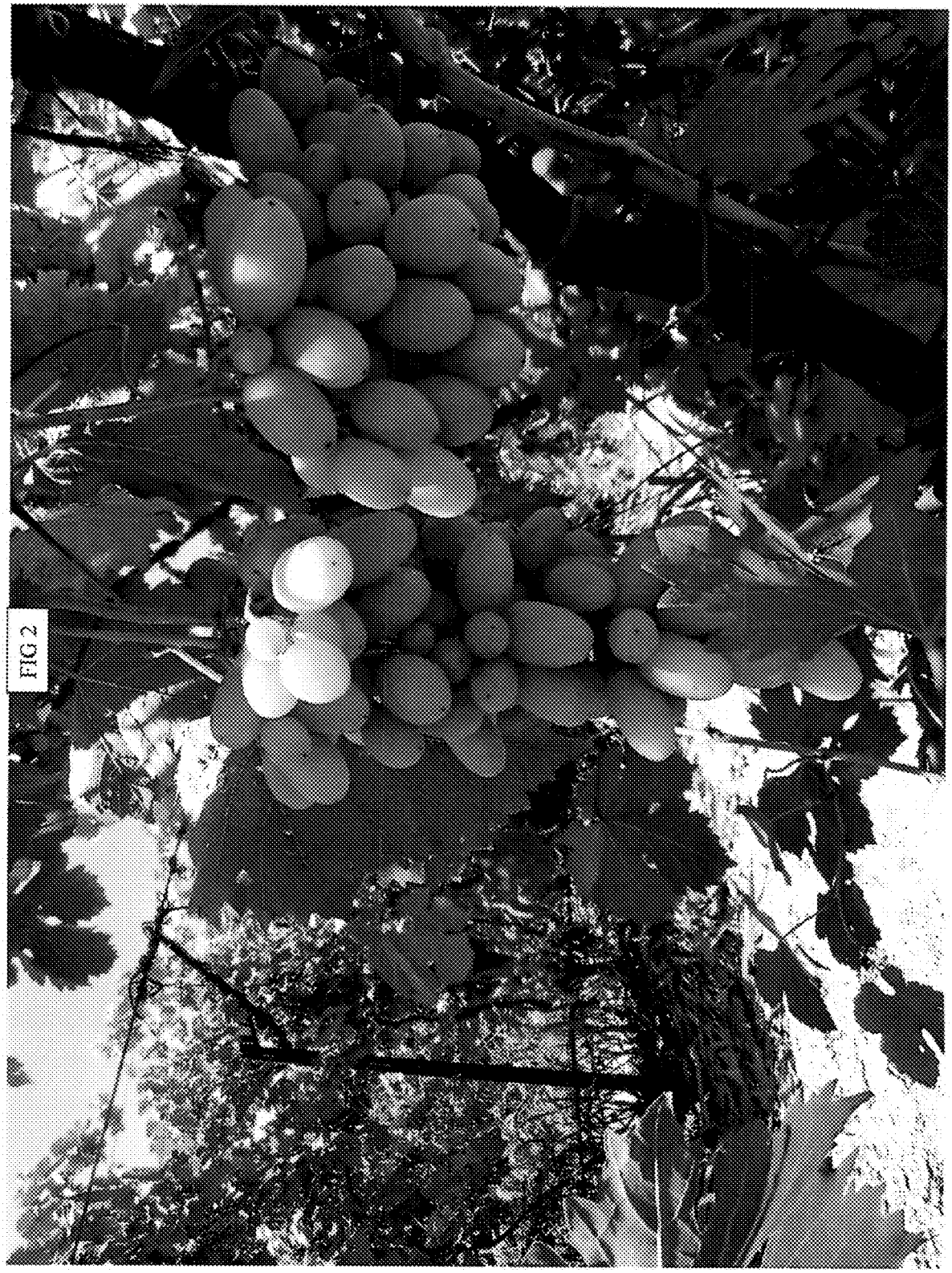
FIG. 2 Fruit clusters on seedling vine of grapevine named SV34-130-92.

The following detailed description sets forth the distinctive characteristics of grapevine named 'SV34-130-92'. Descriptions of the new invention apply to vines of grapevine named 'SV34-130-92' grown on 'Freedom' (unpatented) rootstock at a density of 1,281 vines per hectare grown near McFarland, California in 2022. These vines were in their 4th year of production having been planted in 2017. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV34-130-92'.

Plant:

*Vigor*.—Vines spur-pruned and shoot thinned to 32 shoots average 169.80 cm of growth per cane.
*Density of foliage*.—Moderately dense.
*Hardiness*.—Observed to 0 C.
*Rootstock*.—'Freedom'.
*Bud burst*.—Early.

Trunk:

*Shape*.—Broadly elliptical.
*Straps*.—Long, split.
*Surface texture*.—Shaggy.
*Trunk circumference*.—32.18 cm at 1.0 m of height.
*Inner bark color*.—RHS Greyed-Orange group 165A.
*Outer bark color*.—RHS Greyed-Orange group 166B.

Young leaves:

*Upper surface*.—Color: RHS yellow green group 144A.
*Lower surface*.—Color: RHS yellow-green group 144A Anthocyanin coloration: Absent Density of prostrate hairs between veins on lower surface: Absent. Density of erect hairs between veins of lower surface: Sparse, restricted to the junction of main veins.

Mature leaves:

*Average blade length*.—16.7 cm.
*Average blade width*.—20.4 cm.
*Size of blade*.—Large.
*Shape*.—Pentagonal.
*Number of lobes*.—5.
*Anthocyanin coloration of main veins on the upper side of the blade*.—Absent.
*Mature leaf profile*.—Margin of leaf undulating with leaf tip pointing upward from plane of leaf blade.
*Blistering* (*upper surface*).—Absent.
*Leaf blade tip*.—Ranges from narrowly acuminate to broadly acuminate.
*Margins*.—Lobed, serrate, undulating.
*Apex*.—Broadly acuminate.
*Bases*.—Sagittate.
*Thickness*.—Medium.
*Undulation of blade between main and lateral veins*.—Present.
*Shape of teeth*.—Conical, both sides convex.
*Length of teeth*.—10.7 mm.
*Width of teeth*.—10.1 mm.
*Ratio length/width of teeth*.—10.7:10.1.
*General shape of petiole sinus*.—Open wide.
*Tooth at petiole sinus*.—Absent.
*Petiole sinus limited by veins*.—Absent.
*Shape of upper lateral sinus*.—Strongly overlapping.
*Prostrate hairs between veins* (*lower surface*).—Absent.
*Erect hairs between veins* (*lower surface*).—Absent.
*Prostrate hairs on main veins* (*lower surface*).—Present.
*Density of erect hairs on main veins* (*lower surface*).—Medium density.
*Prostrate hairs on main veins* (*upper surface*).—Present.
*Upper surface*.—Summer color: RHS green group 137A. Surface texture: Smooth. Surface appearance: Dull. Goffering of blade: Absent.
*Lower surface*.—Summer color: RHS green group 137C. Anthocyanin coloration of main veins on lower leaf surface: Absent. Anthocyanin coloration on laterals: Absent. Glossiness: Low. Pubescence: Absent. Surface texture: Rough. Surface appearance: Dull.
*Petiole*.—Length: 13.8 cm. Length of petiole compared to middle vein: About equal. Density of prostrate hairs: Absent. Density of erect hairs: Absent. Shape of base of petiole sinus: Open. Color: In shade: RHS yellow-green group 145A. In sun: RHS yellow-green group 144C.

Tendrils:

*Number & pattern*.—Bifurcated and trifurcated; Continuous after 5th node.

*Length*.—24.4 cm.

*Diameter*.—2.8 mm.

*Texture*.—Smooth.

*Color*.—RHS yellow-green group N144A.

Growing tips (young shoot):

*Pubescence*.—Present, prostrate.

*Color*.—RHS yellow-green group 144A.

*Anthocyanins*.—Absent.

*Shape*.—Rounded.

*Apex*.—Open, fully.

*Shoot attitude*.—Semi-erect.

Green summer shoots:

*Internode color upper surface*.—RHS yellow-green group 152B.

*Internode color lower surface*.—RHS yellow-green group 146B.

*Node color upper surface*.—RHS yellow-green group 146B.

*Node color lower surface*.—RHS yellow-green group 146C.

*Density of erect hairs on internodes*.—Absent.

Woody shoot:

*Canes*.—Shape: elliptical. Internode length: 10.16 cm. Internode diameter: 1.28 cm. Width at node: 2.33 cm. Surface: smooth. Main color: RHS Greyed-Orange group 166C.

*Buds*.—Shape: Conical. Length: 6.5 mm. Width: 5.9 mm. Height: 5.0 mm. Color: RHS Greyed-Orange group 166B.

*Laterals*.—Shape: Broadly sagittate. Number: 1-2. Length: 35.2 cm. Diameter: 6.3 mm. Internode length: 5.8 cm. Color: RHS yellow-green group 147B.

Flowers:

*Flower sex*.—Perfect.

*Position of first flowering nodes*.—4th node.

*Number of inflorescences per shoot*.—1 to 2.

*Calyptra color*.—RHS yellow-green group 144B.

*Ovary length*.—1.8 mm.

*Ovary width*.—1 mm.

*Ovary color*.—RHS yellow-green group 144A.

*Filament length*.—2.8 mm.

*Filament color*.—Translucent, absence of pigmentation.

*Anther length*.—0.7 mm.

*Anther color*.—RHS greyed-orange group N167C.

*Date of full bloom*.—May 3, 2024.

Fruit:

*Ripening period*.—Early July.

*Date of ripening*.—Jul. 7, 2024 near McFarland, California.

*Soluble solids*.—20 degrees brix, Jul. 8, 2024.

*Use*.—Fresh market.

*Keeping quality*.—Very good.

*Shipping quality*.—Good.

*Refractometer test*.—21.0 brix.

*Bunch*.—Size: Medium. Length (peduncle excluded): 24.5 cm. Width: 15.6 cm. Weight: Natural, without gibberellic acid treatment: 425 g. With gibberellic acid treatment: 240 g. Density: Well filled, loose. Number of berries: Natural-129, Gibberellic-67. Form: Conical.

*Peduncle*.—Length: 3.6 cm. Lignification: None Color: RHS yellow-green group 144A.

*Berry*.—Size: Medium. Uniformity of size: Not uniform. Weight Natural, without gibberellic acid treatment: 3.22 g. With gibberellic acid treatment: 3.36 g. Shape: Natural, without gibberellic acid treatment: Oblong. With gibberellic acid treatment: Oblong. Presence of seeds: Seedless with rudimentary seeds. Cross section: Circular. Dimensions: Longitudinal axis: Natural: 2.4 cm. Gibberellic: 2.8 cm. Horizontal axis: Natural: 1.5 cm. Gibberellic: 1.6 cm. Skin color (without bloom): RHS yellow-green group 144C. Coloration of flesh: RHS yellow-green group 145C. Berry flesh anthocyanin coloration: Absent. Juiciness of flesh: Very juicy. Berry firmness: Medium. Bloom (cuticular wax): Weak. Pedicel length: (Samples=8, 6 mm, 7 mm, 13 mm, 12 mm, 6 mm, 8 mm, 8 mm, 4 mm, 6 mm). Berry separation from pedicel: Difficult. Particular flavor: Muscat.

*Skin*.—Thickness: Medium. Texture: Tender, crisp. Reticulation: Absent. Roughness: Absent. Tenacity: Tenacious to flesh. Tendency to crack: Resistant.

Disease and insect resistance: No particular resistance or susceptibility has been observed.

Having thus described and illustrated my new variety of grapevine, I claim:

1. A new and distinct variety of grapevine plant named 'SV34-130-92', substantially as illustrated and described herein.

* * * * *